(12) United States Patent
Kern et al.

(10) Patent No.: US 6,206,836 B1
(45) Date of Patent: Mar. 27, 2001

(54) BATTERY-OPERATED DEVICE, IN PARTICULAR A BLOOD PRESSURE MEASURING DEVICE

(75) Inventors: Alfred Kern, Inning a.A.; Roland Schirrmacher, Graefelfing, both of (DE)

(73) Assignee: Microlife Investments Corporation (TW)

( * ) Notice: Subject to any disclaimer, the term of this patent is extended or adjusted under 35 U.S.C. 154(b) by 0 days.

(21) Appl. No.: 09/369,198

(22) Filed: Aug. 6, 1999

(30) Foreign Application Priority Data

Aug. 11, 1998 (DE) .......................................... 298 14 433 U

(51) Int. Cl.⁷ .............................. A61B 5/02; H01M 2/10; H01M 2/04; H01M 2/02; H01M 2/00
(52) U.S. Cl. ............................ 600/485; 600/481; 429/96; 429/99; 429/100; 429/163; 429/175; 429/176
(58) Field of Search ................................... 600/481, 485; 429/163, 175, 176, 153, 96, 97, 98, 99, 100

(56) References Cited

FOREIGN PATENT DOCUMENTS

| 1 220 503 | 7/1966 | (DE) . |
|---|---|---|
| 72 05 013 | 5/1972 | (DE) . |
| 26 26 707 | 12/1977 | (DE) . |
| 26 40 961 | 3/1978 | (DE) . |
| 91 05 951 | 9/1991 | (DE) . |
| 43 23 455 | 1/1994 | (DE) . |
| 295 19 209 | 4/1996 | (DE) . |
| 296 01 587 | 5/1996 | (DE) . |

OTHER PUBLICATIONS

International Search Report.

*Primary Examiner*—Cary O'Connor
*Assistant Examiner*—N. Natnithithadha
(74) *Attorney, Agent, or Firm*—Shoemaker and Mattare, Ltd.

(57) ABSTRACT

A battery-operated device, for example, a blood pressure measuring device, consists essentially of a housing (2) and a compartment (3) to accommodate batteries. The compartment (3) is rotatably hinge-connected to the housing (2). The compartment (3) can be pivoted between an insertion position (E) for receiving batteries and an operating position (B). The device (1) has a standing surface (15). The compartment (3) for accommodating batteries is arranged so that the outside surface (4) of the compartment (3) in the operating position (B) forms part of one of the side walls (16a, 16b, 16c), and the inside (8) of compartment (3) is open at the top to receive batteries in the insertion position (E).

11 Claims, 3 Drawing Sheets

BATTERY-OPERATED DEVICE, IN PARTICULAR A BLOOD PRESSURE MEASURING DEVICE

BACKGROUND OF THE INVENTION

This invention concerns a battery-operated device, in particular a blood pressure measuring device. Battery-operated devices are used today in a variety of different applications. Such devices generally have a housing with a compartment to accommodate batteries in one location. In most cases, a cover is provided by means of which the battery compartment can be closed.

In addition to devices of electronic entertainment, computers or measurement instruments, medical diagnostic devices for home use today are often battery-operated. For example, there are known blood pressure measuring devices with which electric power supplied by batteries is used to operate a pump as well as the electronic analysis and display units.

Handling can often be a problem when using batteries, especially with such medical devices which are often used by the elderly, and in particular, the conventional flaps that are used to close the battery compartment are often difficult to handle. There is also the problem that the flap may be attached improperly, so that the batteries can drop out again.

SUMMARY OF THE INVENTION

Therefore, one object of the present invention is to avoid the disadvantages of the known device and thus to create a battery-operated device, in particular a blood pressure measuring device, which will allow simple insertion of the batteries and will nevertheless permit a secure seating of the batteries in the housing. Another object of the present invention is to create a battery-operated device such as a blood pressure measuring device which is reliable and can be manufactured economically and easily.

According to this invention, these objects are achieved with a device as described below.

This invention is described here and below on the basis of a blood pressure measuring device. The advantages of this invention are manifested especially clearly with a blood pressure measuring device which is often used by the elderly. It is self-evident, however, that these features would also be advantageous with other battery-operated devices.

The blood pressure measuring device consists essentially of a housing which is provided with electric and/or electronic components. A blood pressure measuring device here includes in particular a pump for inflating a cuff for measuring the blood pressure and pressure measurement sensors plus electronic analysis and display components. Those skilled in the art will be familiar with the electric and electronic components of such a blood pressure measuring device, so these components need not be described in detail here.

This blood pressure measuring device has a compartment to accommodate at least one battery. The compartment is designed to accommodate known standard batteries. The number of batteries will depend on the power requirements of the blood pressure measuring device.

According to this invention, the compartment for accommodating the battery or batteries is rotatably hinge-connected between an insertion position and an operating position on the housing of the blood pressure measuring device. In the operating position, the compartment is closed, and the outside of the compartment forms part of the outside wall of the housing. In the insertion position, the compartment is open, so that batteries can be inserted into the compartment. The compartment for accommodating the batteries is designed as a door or flap. With the flap opened, the batteries can be inserted. When the batteries are inserted, the flap can be closed.

In a preferred embodiment, the device is provided with means for closing an electric contact. These means are designed so that the contact is closed when the compartment is in the operating position. The advantage is that after inserting the batteries and closing the compartment, the electric contact is closed automatically.

Designing the compartment as a rotatable flap has various advantages. For example, the blood pressure measuring device can be operated easily with one hand, and the batteries can be replaced or inserted with one hand. The flap always remains attached to the rest of the housing, and the position of the flap with respect to the housing is therefore defined clearly. The flap can be opened with one hand, and the battery or batteries can be inserted individually into a holder inside the compartment. As soon as all the batteries have been inserted into the compartment, the compartment can be closed again by simply turning it with one hand.

One-handed operation is especially advantageous in conjunction with this blood pressure measuring device in particular. For example, batteries can be inserted even when the cuff has already been placed around the user's arm.

The compartment which is rotatably hinge-connected to the housing also prevents loss or improper attachment of the cover for closing the battery compartment, which is possible with the state of the art.

The means for closing the electric contact may be designed as contact elements especially easily.

The first contact elements are arranged on the compartment to accommodate the battery, and second contact elements are arranged on the housing. In the operating position, i.e., when the compartment is closed, the first and second contact elements are in contact with one another. In this way, an electric circuit is closed and the blood pressure measuring device is ready for operation.

The compartment to accommodate the battery is preferably designed so that it can be snapped into the housing in the operating position. The compartment may be rotatably attached to the housing on one side, for example, and provided with an elastic strap on the opposite side, so the strap can be engaged with a recess in the housing.

This blood pressure measuring device is advantageously designed as a portable device which has one standing surface plus several side surfaces. The compartment to accommodate the batteries is advantageously designed so that the outside of the compartment in the operating position at least partially forms one of the side surfaces of the blood pressure measuring device. The axis of rotation about which the compartment can be rotated is advantageously arranged next to the standing surface. This design guarantees easy insertion and replacement of batteries without having to raise or rotate the entire device. The compartment for accommodating the batteries can be tilted downward when the battery-operated blood pressure measurement device is standing on the standing surface. The receptacle openings for the batteries are then pointing upward, so that batteries can be inserted especially easily.

This device, in particular the housing and the compartment for accommodating the batteries, are advantageously made of a plastic material. The individual parts may be produced by an injection molding process, for example. To create an electric contact between several batteries and between the batteries and the housing, metallic contact strips may be inserted into recesses provided for this purpose in the individual parts.

In addition, the housing is advantageously designed so that the outside of the battery compartment in the operating position and the standing surface form an angle between 45° and 90°, preferably between 65° and 75°.

It is especially easy to open the battery compartment because the outside faces upward in the operating position and is readily accessible from above. Such an arrangement is also advantageous with a battery compartment which is designed as a recess to accommodate batteries in the housing.

This recess may be closed with a flap which need not necessarily be hinge-connected to the housing.

The housing also advantageously has a display and operating field arranged at an angle of approximately 45° to 25°, preferably about 35° to the standing surface.

The standing surface, the display and operating field, the outside of the flap and the battery compartment define an approximately triangular side view of the housing. If the standing surface is selected to be the longest of the side surfaces, this yields an especially good stability of the device. The top side of the device with the operating and display field is selected as the second longest side surface, which makes the display field especially easy to read.

BRIEF DESCRIPTION OF THE DRAWINGS

This invention is explained in greater detail below on the basis of drawings wherein.

DESCRIPTION OF THE PREFERRED EMBODIMENT(S)

Figure 1:
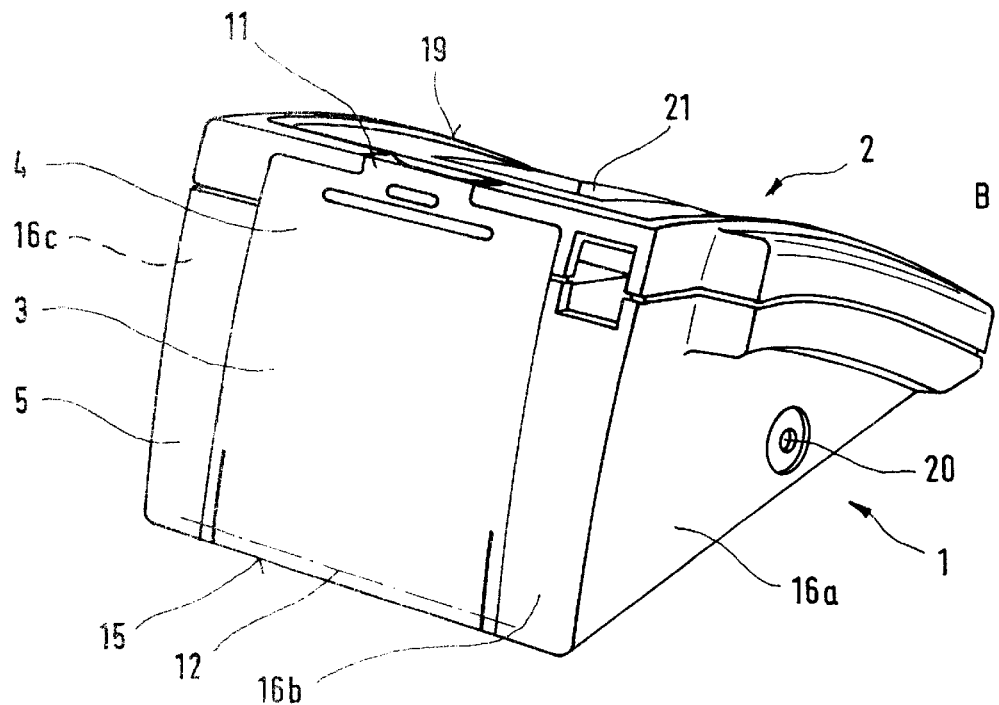
FIG. 1 is a perspective view of the blood pressure measuring device with the compartment for accommodating the batteries closed.

FIG. 1 shows a perspective view of a blood pressure measuring device 1. The blood pressure measuring device 1 consists essentially of a housing 2 and a compartment 3 which serves to hold the batteries. The compartment 3 is rotatably hinge-connected to housing 2 so that it can rotate about an axis 12 of rotation. FIG. 1 shows the blood pressure measuring device 1 in an operating position B. In operating position B, the outside 4 of compartment of 3 forms a part of the outside wall 5 of housing 2. The housing 2 has a recess 18 (see FIG. 2) for the compartment 3, so that compartment 3 can be retracted and the outside 4 of compartment 3 forms a smooth outside wall together with the outside wall 5 of the housing. The outside forms a flap for closing the battery compartment.

The blood pressure measuring device 1 has a standing surface 15 with which it can be placed on a substrate such as a table. The blood pressure measuring device 1 also has three side surfaces 16a, 16b, 16c and one top side 19. Compartment 3 is hinge-connected to the housing 2 so that its outside 4 forms a part of one of the side surfaces 16a, 16b, 16c (in FIG. 1 it forms the essential part of side surface 16b). Axis 12 of rotation is arranged next to the standing surface 15.

The blood pressure measuring device 1 is also provided with a connection 20 for accommodating a pressure hose and with an operating field 21 with operating and display elements. However, the operating and display elements as well as the connection for a pressure hose are not the object of the present invention.

Figure 2:
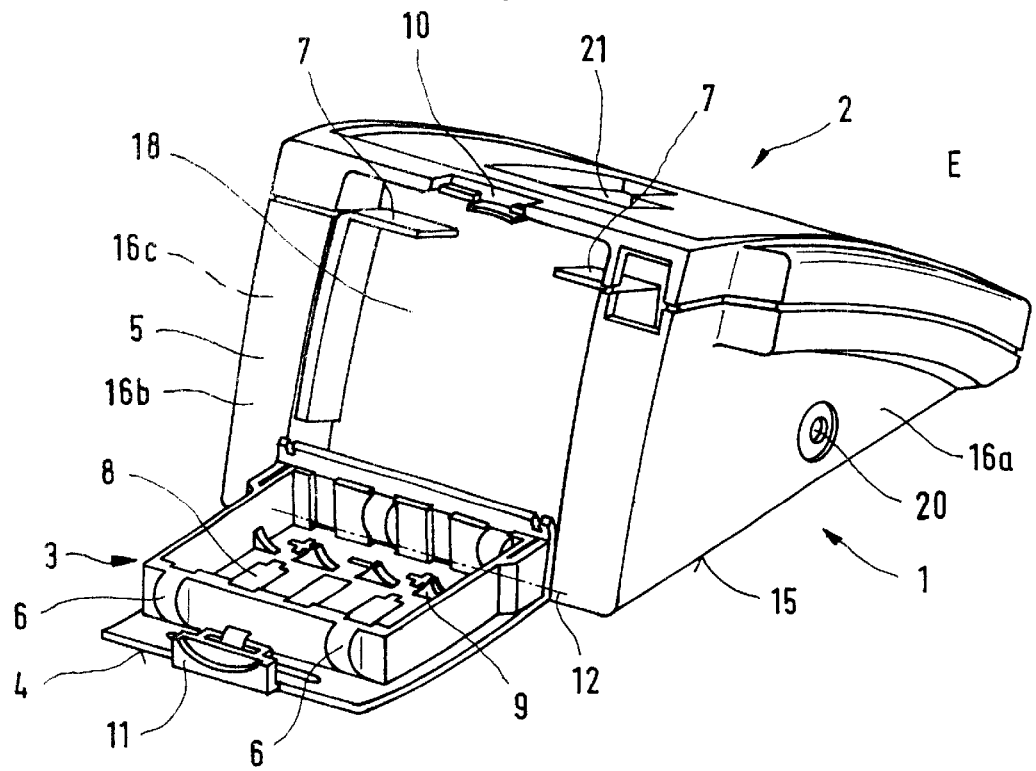
FIG. 2 is a perspective view of the blood pressure measuring device with the compartment for accommodating the batteries closed.

FIG. 2 shows the blood pressure measuring device 1 in a insertion position E. Compartment 3 here has been opened, with the outside 4 of the compartment essentially forming the extension of the standing surface 15.

On the inside 8, the compartment 3 is provided with holders 9 to accommodate batteries. In addition, first contact elements 6 for establishing contact with a second contact element 7 are provided on the housing 2. The contact elements 6 are made of metal strips which are inserted into corresponding recess openings 17 in compartment 3. Compartment 3 is also provided with a strap 11. This strap 11 is designed to be elastic and it can be engaged in a corresponding recess 10 in the housing.

When the batteries have been inserted into the opened compartment 3, the compartment 3 can be closed easily by turning it about the axis 12 of rotation, thereby engaging it with strap 11. Then contact elements 6 and 7 are in contact. This closes an electric circuit, and the blood pressure measuring device is now ready for operation. The compartment 3 is then lowered into a recess 18 in the area of the one side surface 16b of the housing 2.

Figure 3:
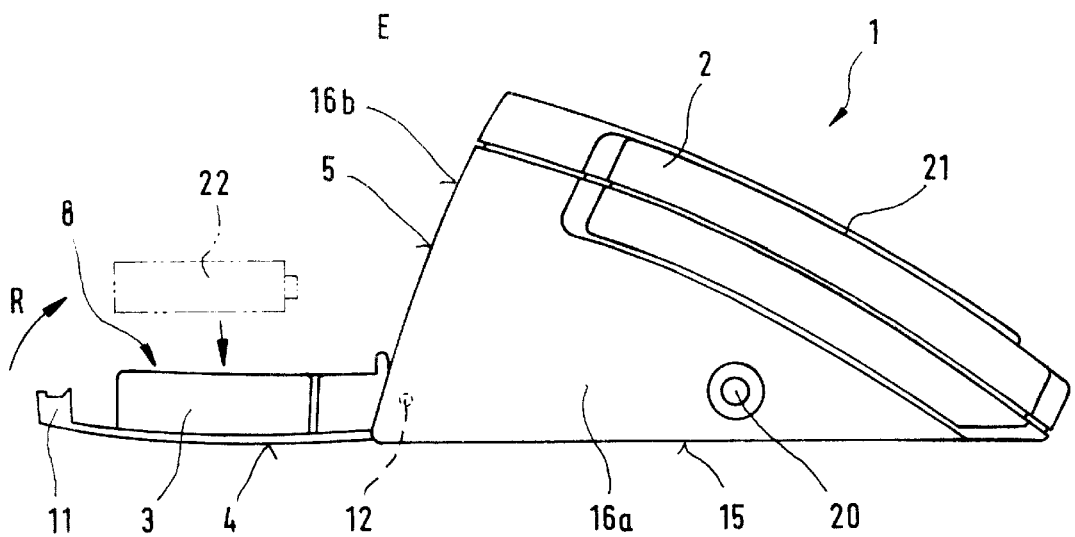
FIG. 3 is a side view of the blood pressure measuring device with the compartment open.

FIG. 3 shows the blood pressure measuring device 1 in the insertion position E, i.e., with the compartment 3 opened. A battery 22, which is shown schematically in this figure, can be inserted easily from above into the compartment 3, which is open at the top. The blood pressure measuring device 1, which is standing with its standing surface 15 on a substrate, therefore need not be turned over to insert or replace batteries. After inserting the battery, the compartment 3 can be closed by rotating about the axis 12 of rotation in the direction of the arrow R. The side surface 16b is arranged at an angle α of 70° to the standing surface 15. The surface 19 with the display and operating field 21 stands at an angle β of 35° to the standing surface 15.

Figure 4:
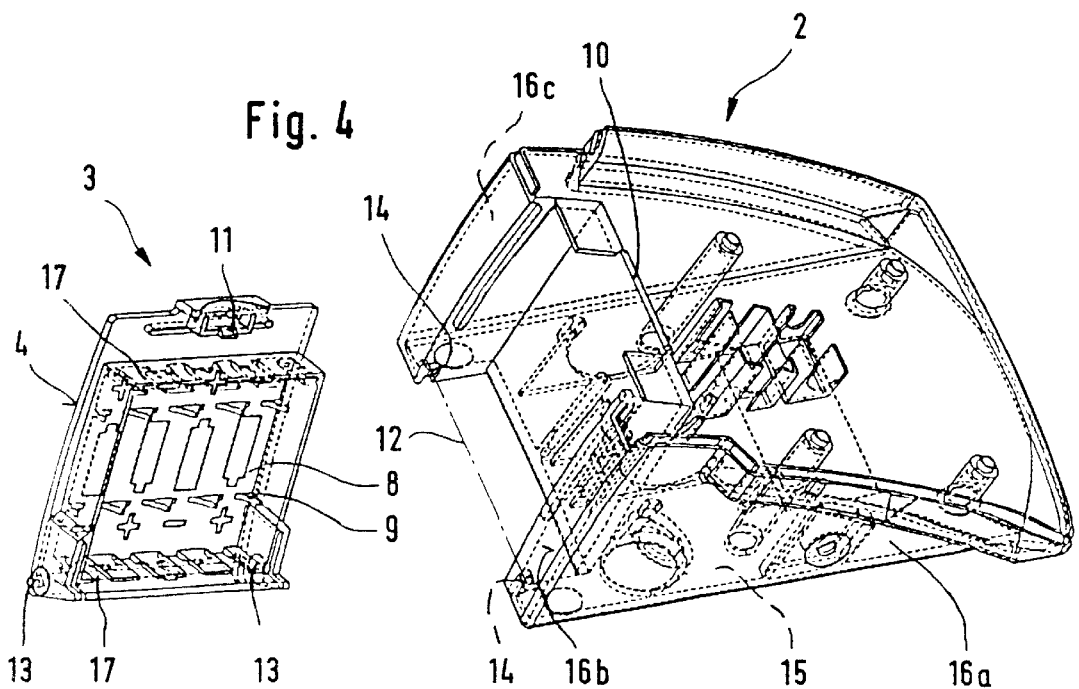
FIG. 4 is a perspective view of a blood pressure measuring device with the compartment for accommodating the batteries shown separately.

FIG. 4 shows the compartment 3 and the housing 2 of the blood pressure measuring device in detail, shown here as separate parts. Recesses 14 in the housing 2 adjacent to the standing surface 15 serve to accommodate cams 13 at one end of the compartment 3. The compartment 3 can thus be rotated about the axis 12 of rotation, which is defined by the recesses 14.

FIG. 4 also shows the holders 9 for the accommodating the batteries in a precisely defined position and the recess openings 17 for accommodating contact elements 6.

The housing 2 has various built-in elements to accommodate the electric and electronic components of the blood pressure measuring device shown here.

The individual parts are manufactured from a plastic material by an injection molding process, for example. Typically, four batteries of the AA/AM3 type are used. The compartment 3 can be engaged in the openings 14 on housing 2, so that no parts such as separate screws or pins are necessary.

Of course, there are many possibilities for designing the device according to the present invention. It is essential that the compartment 3 for the batteries must be designed so that the batteries can be inserted easily from above.

Figure 5:
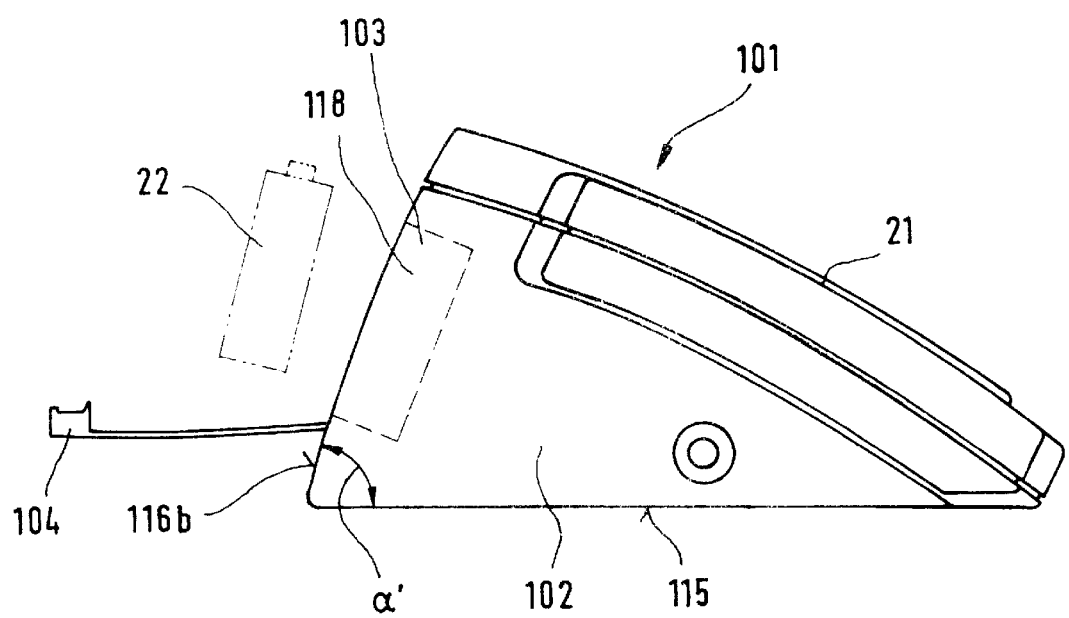
FIG. 5 is a schematic diagram of an alternative embodiment.

FIG. 5 shows a schematic diagram of an alternative embodiment in a cross section. The blood pressure measuring device 102 here is designed like that in the preceding examples, differing only in the design of the battery compartment 103. A battery compartment 103 is integrated as a recess 118 into the one side wall 116b. The compartment 103 may be closed with a flap 104. The flap 104 is hinge-connected to the housing 102 in FIG. 5, but it could also be inserted individually.

The side surface 116b and the flap 104 (when closed) are arranged at an angle α' of approximately 70° to the standing surface 115. Batteries 22 can simply be inserted from above without having to turn the device over. Due to the inclination of side surface 116b, batteries can even be inserted by a user who is on the side of the display and operating field.

What is claimed is:

1. A battery-operated blood pressure measuring device, comprising a housing with an outside wall and with electrical components arranged therein
    and having a compartment for accommodating at least one battery,
    wherein said compartment for accommodating said at least one battery is rotatably hinge-connected to said housing in such a way that it is able to be rotated between an insertion position and an operating position,
    whereby said compartment has an outer surface forming a part of the outside wall of the housing in the operating position and
    whereby said at least one battery is insertable into the compartment in the insertion position.

2. A device according to claim 1, wherein the device has means for closing an electric contact, said means being designed in such a way that the contact is closed when the compartment is in the operating position.

3. A device according to claim 2, wherein said means for closing an electric contact consist of at least a first contact element on the compartment and at least one second contact element on the housing, with the first contact element and the second contact element being in contact with one another in the operating position.

4. A device according to claim 1, wherein the compartment is adapted to be snapped into a recess in the housing when it is in the operating position.

5. A device according to claim 1, wherein the device has a standing surface and side surfaces wherein in the operating position, the compartment with its outside surface forms at least a part of one of said side surfaces.

6. A device according to claim 5, wherein said compartment is rotatable around an axis of rotation, with the axis of rotation being arranged adjacent to the standing surface.

7. A device according to claim 1, wherein the housing and the compartment are substantially made of a plastic material.

8. A battery-operated blood pressure measuring device comprising a display and operating field and a compartment adapted to be closed by a flap and to accommodate at least one battery, and a standing surface, wherein said flap is arranged at an angle between 45° and 80°, to the standing surface when said compartment is closed by said flap.

9. A blood pressure measuring device according to claim 8, wherein said flap is arranged at an angle of approximately 70° to the standing surface when said compartment is closed by said flap.

10. A blood pressure measuring device according to claim 8, wherein said display and operating field is arranged at an angle of 25° to 45° to said standing surface, said standing surface, display field and flap forming substantially the shape of a triangle.

11. A blood pressure measuring device according to claim 10, wherein said standing surface borders the longest housing side, said display and operating field borders the second longest side, and said flap borders the third longest side of the housing.

* * * * *